United States Patent
Gerber et al.

(10) Patent No.: US 7,611,483 B2
(45) Date of Patent: Nov. 3, 2009

(54) INDICATOR METRICS FOR INFECTION MONITORING

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/737,180

(22) Filed: Apr. 19, 2007

(65) Prior Publication Data

US 2008/0262322 A1    Oct. 23, 2008

(51) Int. Cl.
*A61M 31/00* (2006.01)

(52) U.S. Cl. .................. 604/65; 604/66; 604/891.1; 604/502; 604/503

(58) Field of Classification Search .......... 604/65, 604/31, 502, 503–505, 66, 890.1, 891.1; 600/549, 300; 607/6
See application file for complete search history.

(56) References Cited

U.S. PATENT DOCUMENTS

| | | | |
|---|---|---|---|
| 5,029,582 A | 7/1991 | Lekholm | |
| 5,181,905 A | 1/1993 | Flam | |
| 5,546,955 A | 8/1996 | Wilk | |
| 5,807,270 A | 9/1998 | Williams | |
| 5,820,263 A * | 10/1998 | Ciobanu | ............ 374/111 |
| 6,113,539 A | 9/2000 | Ridenour | |
| 6,135,968 A | 10/2000 | Brounstein | |
| 6,248,080 B1 * | 6/2001 | Miesel et al. | ........ 600/561 |
| 6,282,444 B1 | 8/2001 | Kroll | |
| 6,356,774 B1 | 3/2002 | Bernstein | |
| 6,558,351 B1 | 5/2003 | Steil | |
| 6,963,772 B2 | 11/2005 | Bloom | |
| 6,970,741 B1 | 11/2005 | Whitehurst | |
| 7,049,824 B2 * | 5/2006 | Shabino | ............ 324/464 |
| 2002/0042596 A1 | 4/2002 | Hartlaub | |
| 2003/0032892 A1 | 2/2003 | Erlach | |

(Continued)

FOREIGN PATENT DOCUMENTS

DE    10150343 A1    4/2003

(Continued)

OTHER PUBLICATIONS

U.S. Appl. No. 11/737,173, filed Apr. 19, 2007, Gerber.

(Continued)

*Primary Examiner*—Kevin C Sirmons
*Assistant Examiner*—Deanna K Hall
(74) *Attorney, Agent, or Firm*—Campbell Nelson Whipps

(57) ABSTRACT

A method for monitoring an infection in proximity to an implantable medical device includes monitoring an indicator of infection in proximity to an implanted medical device; determining whether the indicator crosses a first threshold indicative of infection for a first period of time; and issuing a first alert if the indicator crosses the first threshold for the first period of time. The method further includes determining whether the indicator crosses a second threshold indicative of infection for a second period of time. A value associated with the second threshold is less indicative of an infection than a comparable value associated with the first threshold. The second period of time is greater than the first period of time. The method further includes issuing a second alert if the indicator crosses the second threshold for the second period of time. The first and second alert may be the same or different.

21 Claims, 10 Drawing Sheets

U.S. PATENT DOCUMENTS

| | | | |
|---|---|---|---|
| 2003/0194752 A1* | 10/2003 | Anderson et al. | 435/7.2 |
| 2003/0199783 A1 | 10/2003 | Bloom | |
| 2003/0216677 A1 | 11/2003 | Pan | |
| 2004/0066313 A1* | 4/2004 | Ong et al. | 340/870.11 |
| 2005/0012610 A1 | 1/2005 | Liao | |
| 2005/0090761 A1 | 4/2005 | Carney | |
| 2005/0096584 A1 | 5/2005 | Ferek-Petric | |
| 2006/0062852 A1 | 3/2006 | Holmes | |
| 2006/0079793 A1 | 4/2006 | Mann | |
| 2006/0149331 A1 | 7/2006 | Mann | |
| 2006/0224088 A1 | 10/2006 | Roche | |
| 2006/0271108 A1 | 11/2006 | Libbus | |

FOREIGN PATENT DOCUMENTS

| | | |
|---|---|---|
| GB | 2 405 203 | 2/2005 |
| WO | WO 02/068049 | 9/2002 |
| WO | WO 2005/000091 | 1/2005 |
| WO | WO 2005/000160 | 1/2005 |
| WO | WO 2006/013585 | 2/2006 |
| WO | WO 2007/028035 | 3/2007 |

OTHER PUBLICATIONS

U.S. Appl. No. 11/737,176, filed Apr. 19, 2007, Gerber.
U.S. Appl. No. 11/737,181, filed Apr. 19, 2007, Gerber.
U.S. Appl. No. 11/737,179, filed Apr. 19, 2007, Gerber.
U.S. Appl. No. 11/737,171, filed Apr. 19, 2007, Gerber.
U.S. Appl. No. 11/737,170, filed Apr. 19, 2007, Gerber.
U.S. Appl. No. 11/737,169, filed Apr. 19, 2007, Gerber.
Robicsek, F., et al., The value of thermography in the early diagnosis of postoperative sternal wound infections. Thoracic & Cardiovascular Surgeon, 1984, 32(4): p. 260-5.
Saxena, A.K., et al., Thermography of *Clostridium perfringens* infection in childhood. Pediatric Surgery International, 1999, 15(1): p. 75-6.
Waterman, N.G., L. Goldberg, and T. Appel, Tissue temperatures in localized pyogenic infections. American Journal of Surgery, 1969, 118(1): p. 31-5.
PCT International Search Report dated Oct. 10, 2007.
PCT International Search Report dated Dec. 5, 2007.
PCT International Search Report dated Nov. 19, 2007.

* cited by examiner

INDICATOR METRICS FOR INFECTION MONITORING

FIELD

This disclosure relates, inter alia, to implantable medical devices. More particularly, it relates to systems, devices and methods for monitoring infection in proximity to medical devices implanted in patients.

BACKGROUND

Infection associated with implantation of medical devices is a serious health and economic concern. Today, infections associated with implanted medical devices are not very common due to care and precautions taken during surgical implantation of the devices. However, when infection associated with an implanted medical device (IMD) does occur, explanting the device is often the only appropriate course of action.

For IMDs having a battery powered component, such as implantable cardiac pacemakers, cardioverter/defibrillators having pacing capabilities, other electrical stimulators including spinal cord, deep brain, nerve, and muscle stimulators, infusion devices, cardiac and other physiologic monitors, cochlear implants, etc., the battery powered component is typically enclosed in a housing that is implanted subcutaneously at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Accordingly, aggressive systemic drug treatment is prescribed to treat such infections. However, early detection of infection associated with implanted medical devices may allow for earlier intervention, resulting in fewer device explants.

Monitoring of infection through the use of sensors, such as temperature and pH sensors that can provide information indicative of infection, has been proposed. However, the use of such information to monitor infection in subtle and desirable ways does not appear to have been described.

SUMMARY

The present disclosure describes, inter alia, systems, devices and methods that can be used to monitor an infection in proximity to an implanted medical device and issue alerts to the patient, healthcare provider, or the like based on more than one metric associated with information regarding the indicator of infection. The evaluation of the likelihood of infection in proximity to an implanted device using more than one metric allows for more refined monitoring of the infection.

In various embodiments, a method for monitoring infection in proximity to an implanted medical device is described. The method includes monitoring an indicator of infection in proximity to an implanted medical device, determining whether the indicator crosses a first threshold indicative of infection for a first period of time, and issuing a first alert if the indicator crosses the first threshold for the first period of time. The method further includes determining whether the indicator crosses a second threshold indicative of infection for a second period of time. A value associated with the second threshold is less indicative of an infection than a comparable value associated with the first threshold, and the second period of time is greater than the first period of time. The method further includes issuing a second alert if the indicator crosses the second threshold for the second period of time. The first and second alert may be the same or different.

By providing devices, systems and methods that take into account more than one metric associated with an indicator of infection, determinations of whether an infection is in proximity to an implanted medical device may be improved and more finely tailored. For example, it may be desirable to immediately issue an alert if a value associated with an indicator is highly predictive of an infection. However, it may be desirable to delay issuance of an alert if a less predictive value is detected until the less predictive value has been detected over a period of time, and thus is more strongly indicative of an infection. Further, certain detected values may not warrant issuance of an alert, but may warrant closer monitoring of the indicator. Accordingly, the frequency of monitoring of the indicator may be increased to more closely monitor temperature once a threshold metric is detected. Changing of frequency of monitoring as conditions warrant may result in power conservation. By keeping low the frequency with which an indicator if infection is monitored until a threshold metric is detected, power may be saved by not frequently monitoring the indicator at a time where infection is not likely. Power conservation may be particularly beneficial to implanted medical devices having a battery component. These and other advantages will be readily understood from the following detailed descriptions when read in conjunction with the accompanying drawings.

Figure 1:
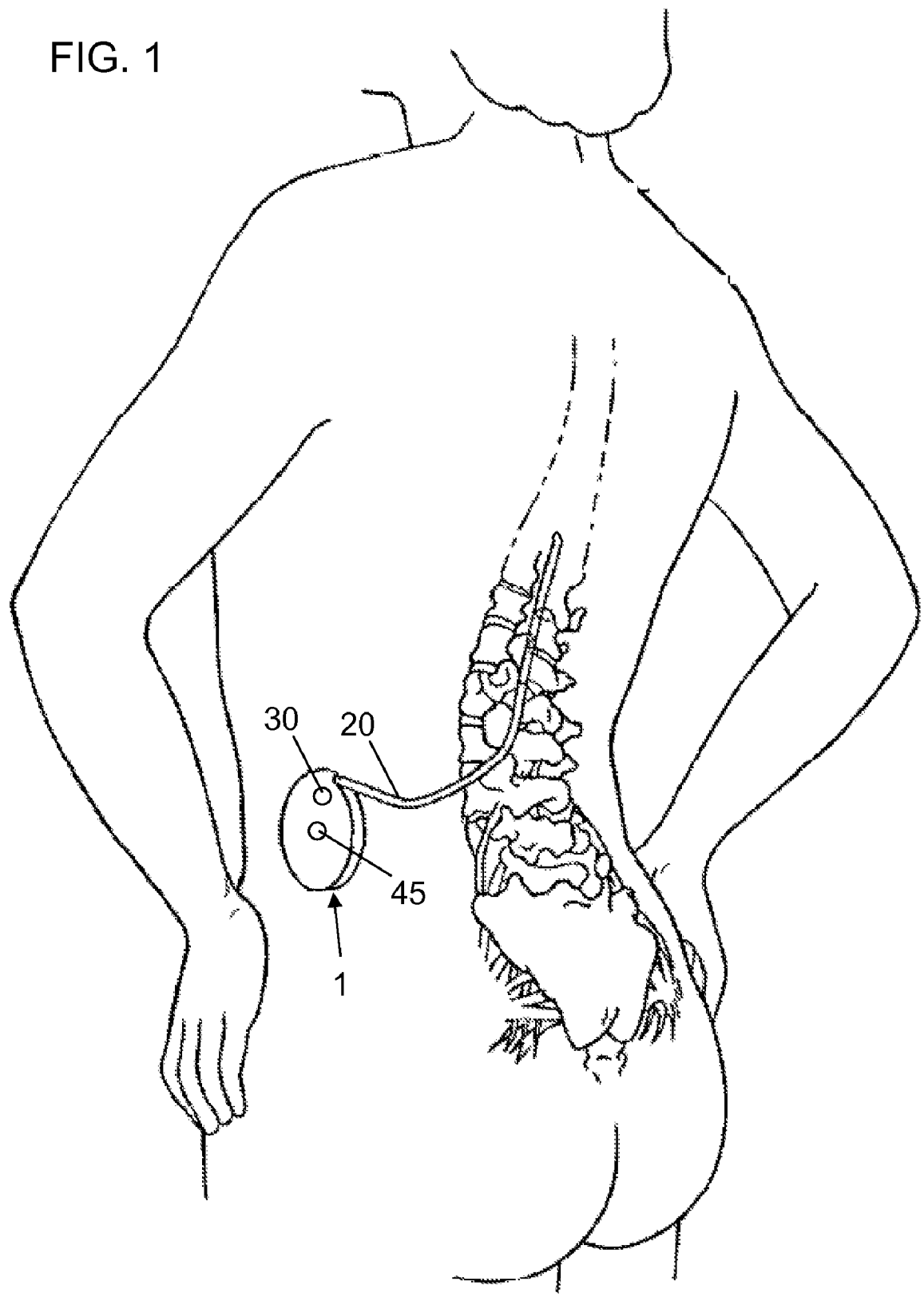
FIG. 1 is a diagrammatic representation of a perspective view of an environment of an implantable infusion system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "active implantable medical device" means an implantable medical device that includes a power source to deliver therapy to a patient. Non-limiting examples of active implantable medical devices include implantable infusion devices and implantable electrical signal generators, such as cardiac defibrillators, pacemakers, neurostimulators, gastric stimulators, and cochlear implants. Active implantable medical devices typically are used in conjunction with associated implantable medical devices, such as catheters or leads.

As used herein, "crosses a threshold", or the like, means meets or exceeds a threshold. It will be understood that a decrease in a value may "exceed" a threshold. For example, if a threshold is a pH of less than 6.5, a pH of 6.4 exceeds the threshold. Similarly, if a threshold is a 10% deviation from a mean value, an 11% negative deviation exceeds the threshold.

As used herein, "comparable value" or the like, in the context of a threshold associated with an indicator of infection, means a value of a type of data the same as the type of data to which it is being compared. For example, a value comparable to a temperature is another temperature. By way of further example, a value comparable to a percent deviation from a mean pH is another percent deviation from a mean pH.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that may be used to monitor infection in proximity to an implanted medical device. The systems, devices and methods determine whether an infection is in proximity to the implantable medical device by using more than one metric associated with a monitored indicator of infection. The evaluation of the likelihood of infection in proximity to an implanted device using more than one metric allows for more refined monitoring of the infection.

The teachings described herein may be employed in conjunction with nearly any implantable medical device, including monitoring devices. In some embodiments described herein, benefit may be seen with active implantable medical devices—i.e., those having a power source for providing therapy, which power source may otherwise be drained by the constant monitoring of infection during time periods where infection is not likely to be observed. For example, in some embodiments, the frequency of monitoring of an indicator of infection is kept low until a threshold value associated with the monitored indicator is crossed, allowing power to be saved by not frequently monitoring the indicator at a time where infection is not likely.

Figure 2:
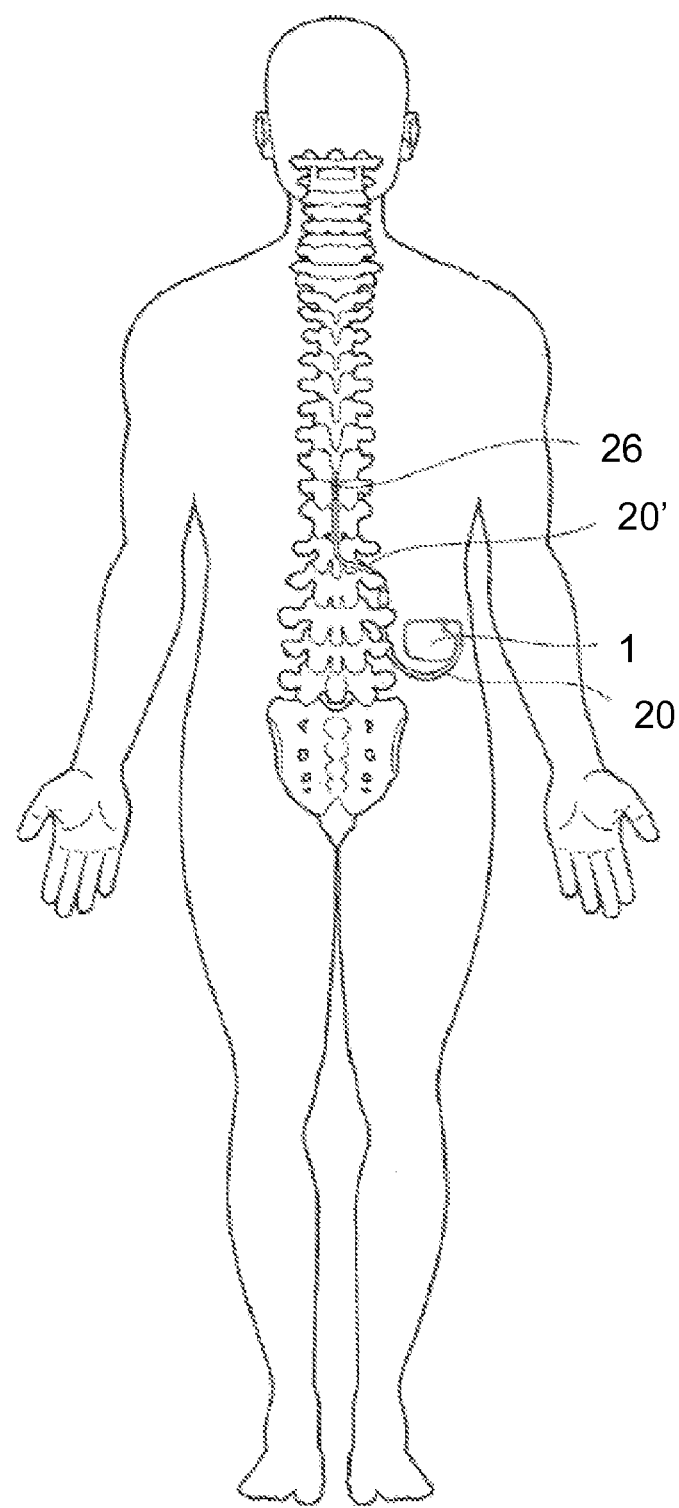
FIG. 2 is a diagrammatic representation of a perspective view of an environment of an implantable electrical signal generator system implanted in a patient.
Figure 3A:
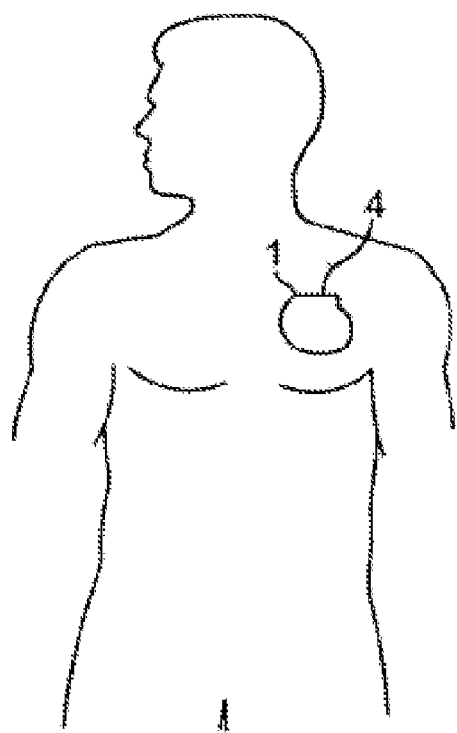
FIGS. 3A-D are a diagrammatic representations of a perspective views of environments of implantable medical devices implanted in patients.
Figure 3B:
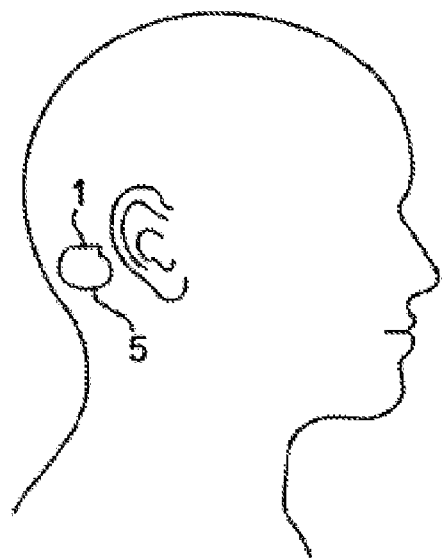
Figure 3C:
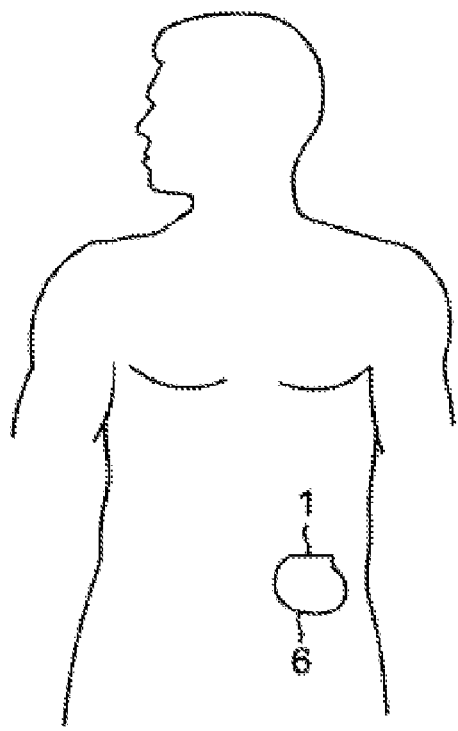
Figure 3D:
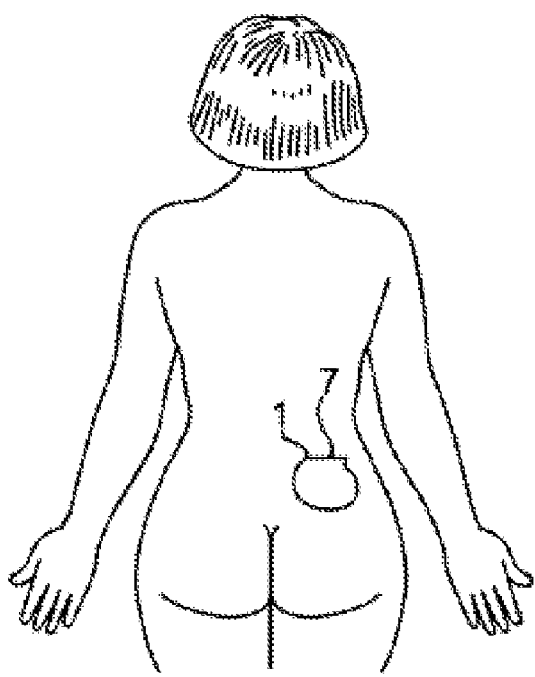

Referring to FIGS. 1 and 2, general representative environments for implanting active medical devices 1 and associated devices 20 are shown. Active medical device 1 is subcutaneously implanted in an abdominal region of a patient. A distal portion of associated device 20 is intrathecally inserted into the patient's spinal canal through a lumbar puncture and advanced rostrally to a desired location (FIG. 1) or epidurally placed along a suitable location of spinal cord (FIG. 2). Proximal end of associated device 20 is tunneled subcutaneously to location of active device 1, where it may be connected to active device 1. While distal portion of associated device 20 is shown in FIGS. 1 and 2 as being located in or on spinal cord, it will be understood that associated device 20 may be placed at any location in patient for which it is desirable to administer therapy generated or delivered by active medical device 1.

In the embodiment shown in FIG. 1, active implantable device 1 is an infusion device, and associated device 20 is a catheter. Catheter 20 is typically a flexible tube with a lumen running from the proximal end of catheter 20 to one or more delivery regions that are typically located at the distal portion of catheter 20. Proximal portion of catheter 20 is connected to infusion device 20. Distal portion of catheter 20 is positioned at a target location in the patient to deliver fluid containing therapeutic agent from infusion device 1 to patient through a delivery region of catheter 20. Infusion device 1, such as Medtronic Inc.'s SynchroMed™ II implantable programmable pump system, includes a reservoir (not shown) for housing a therapeutic substance and a refill port 45 in fluid communication with reservoir. The reservoir may be refilled by percutaneously inserting a needle (not shown) into patient such that needle enters refill port 45, and fluid containing therapeutic substance may be delivered into reservoir from needle via refill port 45. Infusion device 1 shown in FIG. 1 also includes a catheter access port 30 that is in fluid communication with the catheter 20. Fluid may be injected into or withdrawn from patient through catheter 20 via catheter access port 30 by percutaneously inserting a needle into access port 30. Each entry of needle across patient's skin to gain access refill port 45 or access port 30 results in the possibility of infection in proximity to the active medical device 1.

In the embodiment shown in FIG. 2, active implantable device 1 is an electrical signal generator, such as Medtronic Inc.'s Restore™ Advanced implantable neurostimulator, and associated devices 20, 20' are a lead extension 20 and lead 20'. Lead 20' includes one or more electrical contacts (not shown) on its proximal end portion and one or more electrodes on its distal end portion 26. The contacts and electrodes are electrically coupled via wires running through lead 20'. Electrical signals generated by the signal generator 1 may be delivered to lead 20 through the contacts and then to the patient through the electrodes. As shown in FIG. 2, lead 20' may be connected to signal generator 1 through a lead extension 20. Extension 20 includes one or more contacts at the proximal and distal end portions that are electrically coupled through wires running through extension 20. Of course it will be understood that with some systems lead 20' may be directly connected to electrical signal generator 1 without use of a lead extension 20. It will be further understood that more than one lead 20' or lead extension 20 may be employed per signal generator 1.

While FIGS. 1 and 2 depict systems including as active implantable medical devices 1 infusion devices and electrical signal generators, it will be understood that the teachings described herein may be applicable to virtually any known or future developed active implantable medical device and that virtually any non-active implantable medical device may be appropriately adapted and configured to perform according to the teachings provided herein.

Referring to FIG. 3, alternative locations for implanting a medical device 1 are shown. As depicted in FIG. 3A, device 1 may be implanted in the pectoral region 7 of a patient. Alternatively, device 1 may be implanted in the head of a patient, more specifically behind the patient's ear (FIG. 3B), in the patient's abdomen (FIG. 3C) or in the patient's lower back or buttocks (FIG. 3D). Of course, device 1 may be placed in any medically acceptable location in patient.

Figure 4:
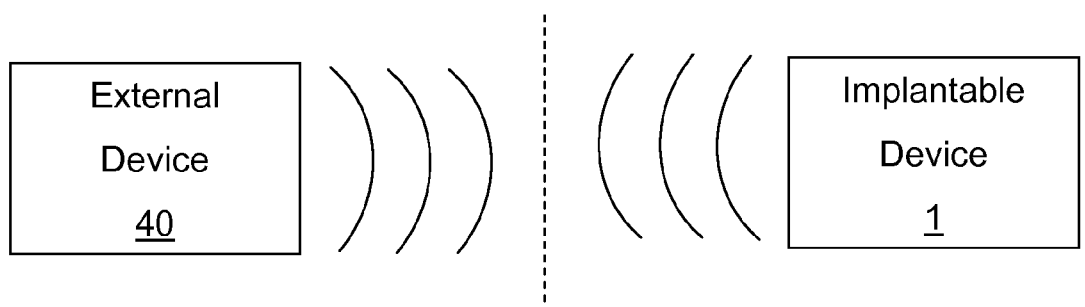
FIG. 4 is a diagrammatic representation of an external device in wireless communication with an implantable medical device.

Referring to FIG. 4, an external device 40 in wireless communication with implantable device 1 is shown. External device 40 may communicate with implantable device 1 through patient's skin, which is represented by the dashed line in FIG. 4. In various embodiments, implantable device 1 carries out the various infection monitoring methods, or portions thereof, described herein. In some embodiments, the combination of implantable device 1 and external device 40 carry out the various infection monitoring methods, or portions thereof, described herein. In various embodiments, where implantable device 1 is a programmable device, external device 40 may be a programmer device, such as Medtronic Inc.'s N'Vision™ clinician programmer. Of course external device may be any device capable of wirelessly communicating with implantable device 1, such as a patient programmer, a computer, a personal data assistant, or the like. External device 40 and implantable device 1 may be capable of one-way (external device 40 to implantable device 1 or implantable device 1 to external device 40) or two-way communication.

Figure 5A:
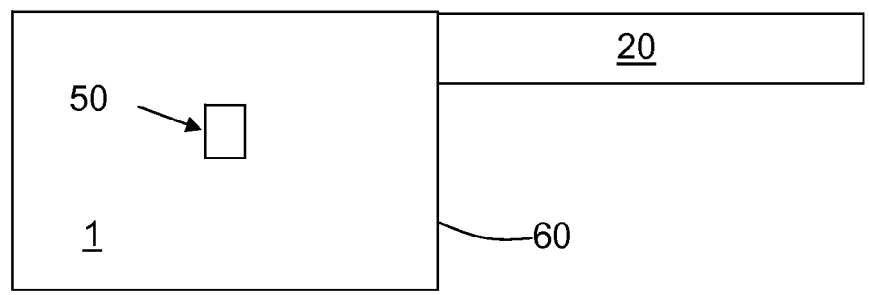
FIGS. 5A-B is a diagrammatic representation of a side view (5A) and back view (B) of an implantable medical device system having sensor(s) in proximity to the implantable device.
Figure 5B:
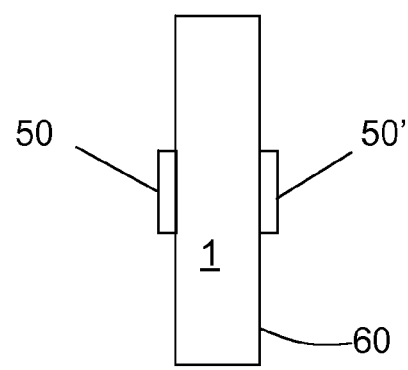

Referring to FIG. 5, sensor(s) 50, 50' associated with implantable active medical device 1 is shown. FIG. 5A is a side view of a representative active device 1 and associated device 20. FIG. 5B is a back view of a representative active device 1. One or more sensor 50, 50' may be located in proximity to device 1; e.g., disposed on, in, or near housing 60 of device 1. Sensor 50, 50' may be any device capable of detecting and transmitting information regarding an indicator of infection to device 1 or capable of detecting and transmitting information that may be useful in determining whether an indicator of infection may actually be indicative of infection. If housing 60 is hermetically sealed, feedthroughs (not shown) may be used to provide electrical connectivity through housing 60 while maintaining the hermetic seal. While not shown, it will be understood that one or more sensor capable of detecting an indicator of infection may be located on, in, or about accessory device 20. Examples of physical or chemical stimuli that may serve as indicators of infection are temperature, impedance, pH, and biological markers of infection. Examples of parameters that may provide information useful for determining whether an indicator of infection may actually be indicative of infection include parameters indicative of patient activity.

Changes in temperature in proximity to implanted device 1 may be used as an indicator of infection in proximity to device 1. The temperature of body tissue at a site of infection is generally greater than that of body tissue at a location removed from the site of infection. Accordingly, an increase in temperature in proximity to an implanted medical device 1 may serve as an indicator of infection. Any suitable sensor 50, 50' capable of detecting temperature or changes in temperature may be employed. For example, temperature sensor 50, 50' may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

Changes in impedance of tissue in proximity to implanted device 1 may be used as an indicator of infection in proximity to device 1. For example, an increase in fluid in tissue is often observed at a site of an infection. Accordingly, a decrease in impedance of tissue in proximity may serve as an indicator of infection. Further, following implantation of device 1, an initial increase in impedance may be expected. Accordingly, failure to detect an increase in impedance over a period of time following implantation may serve as an indication of infection. In the case of impedance measurement, detection or monitoring, sensors 50, 50' are electrodes. Impedance may be measured between two electrodes. Current or voltage is applied between the electrodes with one electrode at any given time serving as a source and the other serving as a sink. In various embodiments, electrodes will be positioned at opposing surfaces of housing 60 of device 1. In other embodiments, one electrode may be located on accessory device 20, e.g. on a lead, and one may be located on housing of device 1. Alternatively, one electrode may be located on accessory device 20 and housing 60 of device 1 may serve as a return electrode, in a manner similar to unipolar signal generators. Further, it will be understood that more than one electrode pair may be employed to monitor impedance. It will also be understood that particular absolute values obtained regarding impedance will vary depending on relative placement and size of the electrodes.

In instances where device 1 is an electrical signal generator, the electrical components used for generating therapeutic electrical signals may also be used for generating signals for impedance monitoring. In instances where device 1 is not an electrical signal generator, e.g. device 1 is an infusion pump, components capable of generating appropriate electrical signals for testing impedance of body tissue may be incorporated into device 1. Any impedance detection components or circuitry may be employed. For example, an ohm meter or a wheatstone bridge design may be used to measure or detect changes in impedance or resistance. Examples of suitable components or circuitry are described in, for example, the following patents and applications assigned to Medtronic, Inc.: US 2006/0259079; US 2006/0036186; US 2004/0162591; US 2003/0176807; U.S. Pat. No. 5,876,353; U.S. Pat. No. 5,824,029; and U.S. Pat. No. 5,282,840.

Changes in pH in proximity to implanted device 1 may be used as an indicator of infection in proximity to device 1. As pH may serve as a general indicator of the state of a tissue, a change in pH may be indicative of infection. Accordingly, a sudden or gradual change in pH in proximity to an implanted medical device 1 may serve as an indicator of infection. Any suitable sensor 50, 50' capable of detecting pH or changes in pH may be employed.

Any biological marker of infection may be detected in accordance with the teachings presented herein. Non-limiting examples of biological markers of infection include viral, fungal, or bacterial proteins or nucleic acids or fragments thereof. As most infections associated with implantable medical devices appear to be due to infection due to *Staphlococcus aureus, Staphlococcus epidermis, Pseudomonus auruginosa* and *Candidia* Sp., detection of proteins, nucleic acids, or fragments thereof of such microorganisms may be beneficial. Alternatively, detection of indicators of an immune response may be detected. For example, an increase in a pro-inflammatory cytokine. Non-limiting examples of proinflammatory cytokines include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Indication of an immune response may also be detected by an decrease in an anti-inflammatory cytokine in proximity to device 1. Non-limiting examples of anti-inflammatory cytokines include IL-4, IL-10, IL-17, IL-13, IL-1α, and TNFα receptor. It will be recognized that some of proinflammatory cytokines may act as anti-inflammatory cytokines in certain circumstances, and vice-versa. Such cytokines are typically referred to as plieotropic cytokines. An immune response may also be detected by measuring changes (baseline versus after device implant or other event, a first point after device implant or other event versus a second point after device implant or other event, etc.) in the presence of other factors involved in an immune response. Non-limiting examples of such other factors include TGF, PDGF, VEGF, EGF, FGF, I-CAM, and nitric oxide. In addition, an immune response may be detected by changes in chemokines, such as 6cKine and MIP3beta, and chemokine receptors, including CCR7 receptor. Further, an immune response may be measured by changes in immune cell population (upregulated Langerhans cells, dendritic cells, lymphocytes), or immune cell surface co-stimulatory molecules (Major Histocompatibility, CD80, CD86, CD28, CD40). An immune response may also be detected by measuring changes in other factors involved in the inflammatory cascade, for example in the signal transduction cascades including factors such as NFκ-B, Egr-1, Smads, toll-like receptors, and MAP kinases. In addition, an immune response may be detected by a change in the presence of an exogenous antigen believed to have caused an inflammatory response, such as, e.g., a bacteria, a virus, or a fungus.

Any sensor capable of detecting such biological markers indicative of infection may be used. In various embodiments, a biosensor is used to detect the presence of a molecule in proximity to implanted device 1. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, sensor 50, 50' includes an electrode with an ion selective coating that is capable of directly transducing the amount of a particular substance. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in Neuroscience Letters, 120 (1990) 249-252. In various embodiments, sensor 50, 50' may be a sensor as described in, e.g., U.S. Pat. No. 5,978,702, entitled TECHNIQUES OF TREATING EPILEPSY BY BRAIN STIMULATION AND DRUG INFUSION or U.S. 2005/0209513, entitled COLLECTING SLEEP QUALITY INFORMATION VIA A MEDICAL DEVICE, filed Apr. 15, 2004, and published Sep. 22, 2005. Modifications of the teachings presented in the above-cited references may be made to account for one or more biological marker of infection.

For certain biological markers, e.g. proteins or nucleic acids or fragments thereof of microorganisms responsible for infection, merely the presence of such markers may be indicative of an infection. For other markers that may be present in a patient lacking an infection, e.g. cytokines and chemokines, increases or decreases in the levels of such markers may be indicative of an infection.

For the above-discussed indicators of infection or other indicator of infection, it may be desirable to compare levels of the indicators at a location in proximity to device 1 and at a location removed from device. Such comparisons may allow for a reduction in false positive detections. For example, elevation in temperature in proximity to device 1 may be due to localized infection or may be due to increased activity of the patient; increases in inflammatory cytokines in proximity to the device may be due to localized infection or a more general immune response; etc. By comparing the level of an indicator of infection in proximity to an implanted device to the level at a location removed from the device, a more accurate determination of whether an infection is present in proximity to the device may be made. Additional information regarding monitoring an indicator of infection at two locations is provided in U.S. patent application Ser. No. 11/737,171, entitled "Implantable Therapy Delivery System Having Multiple Temperature Sensors", filed on even date herewith, naming Martin Gerber and John Rondoni as inventors, which application is hereby incorporated herein by reference in its entirety to the extent it does not conflict with the disclosure presented herein.

Information regarding a first indicator of infection may be used to determine whether an infection is present in proximity to the implanted device 1. In addition, one or more second indicators of infection may be used to determine whether the indication based on the first indicator is accurate. Additional information regarding infection monitoring using two or more indicators of infection is provided in U.S. patent application Ser. No. 11/737,181, entitled "Multi-Parameter Infection Monitoring", filed on even date herewith, naming Martin Gerber and John Rondoni as inventors, which application is hereby incorporated herein by reference in its entirety to the extent it does not conflict with the disclosure presented herein.

Figure 6:
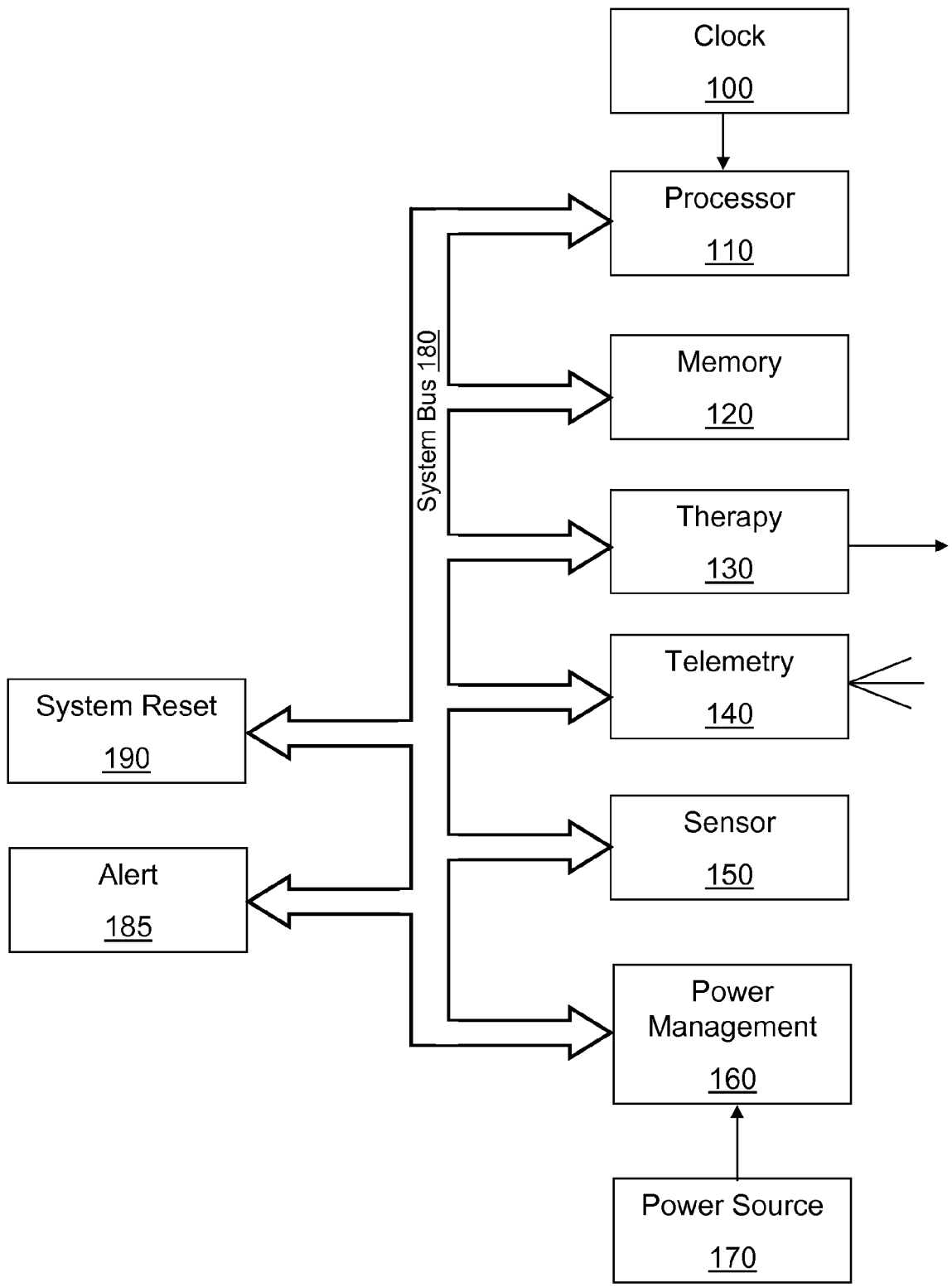
FIG. 6 is a schematic block diagram of representative components of a representative implantable medical device.

Referring to FIG. 6, some representative electronic components of an implantable medical device 1 according to various embodiments are shown in block form. Active implantable medical device 1 as depicted in the embodiment shown in FIG. 6 includes a clock 100, a processor 110, a memory 120, a therapy output or delivery component 130, a telemetry component 140, a sensor 150, a power management module 160, a power source 170, an alert module 185, and a system reset module 190. Other components of active implantable medical device 1 can include, e.g., a diagnostics module (not shown). All components except the power source 170 can be configured on one or more Application Specific Integrated Circuits (ASICs) or may be one or more discrete components, or a combination of both. Also, all components, except the clock and power source are connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 120 includes memory sufficient for operation of device 1, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as telemetry module 140 or sensor module 150, so that the selected modules can request control of data bus 180 and write data directly to memory 120 bypassing processor 110. System Reset 190 controls operation of ASICs and modules during power-up of device 1, so ASICs and modules registers can be loaded and brought on-line in a stable condition.

Telemetry 140 module or other wireless module provides for communication between implantable device 1 and external device 40 such as a programmer. Communication may be bi-directional. Telemetry module 140 generally includes a telemetry antenna, a receiver, a transmitter, and a telemetry processor. Telemetry modules are generally known in the art and are further detailed in U.S. Pat. No. 5,752,977, entitled "Efficient High Data Rate Telemetry Format For Implanted Medical Device" issued to Grevious et al. (May 19, 1998), which is incorporate herein by reference in its entirety to the extent that it does not conflict with the disclosure presented herein. While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 130 refers to components for carrying out the delivery or generation of therapeutic output to be delivered to a patient from active device 1. One of skill in the art will appreciate that the components may vary on a device-by-device basis and a therapy-by-therapy basis. For example, therapy module 130 may contain an oscillator if device 1 is an electrical signal generator and may contain a pumping mechanism if device 1 is an infusion device.

Sensor module 150 includes a sensor 50, 50', e.g. as discussed with regard to FIG. 5, and may include other components for transmitting sensed information from sensor 50, 50' to, e.g., processor 110 or memory 120. Sensor module 150 or other components of device 1 may include one or more analog to digital converters to convert analog signals generated by sensor 50 into digital signals usable by processor 110, as well as suitable filter and amplifier circuitry.

Alert module 185 may issue an alert, e.g. an audible alert or tactile alert, such as a vibration. An alert may be issued if information indicative of an infection is detected. The alert will serve to prompt the patient to seek medical attention.

Figure 7:
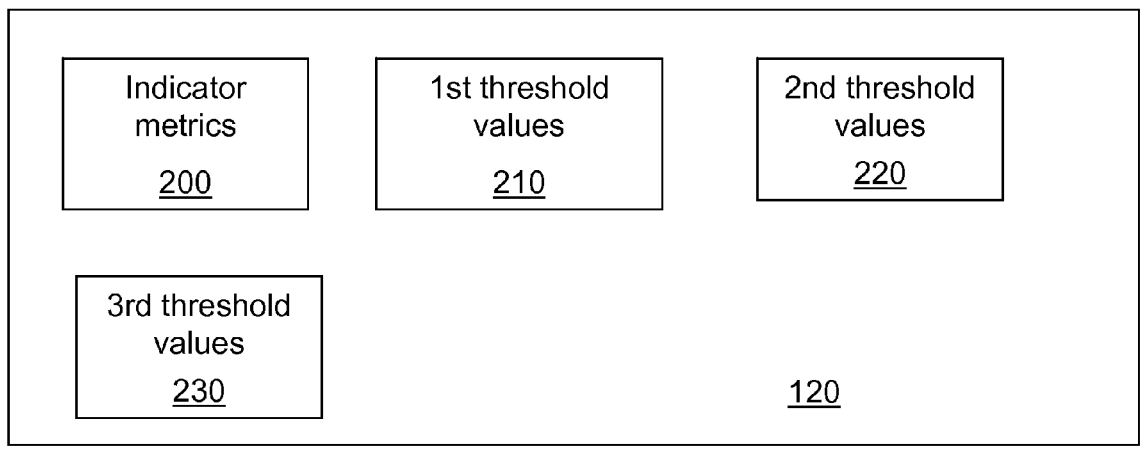
FIG. 7 is block diagram of portions of a representative memory.

Referring to FIG. 7, memory 120 is shown in more detail. According to various embodiments, memory 120 stores information related to indicator of infection 200, first threshold values 210, and second threshold values 220. Memory may also store information regarding third threshold values 230. Threshold values 210, 220, 230 may be values specified by an external device 40, such as a physician programmer, and may be specifically tailored to a particular patient. Information stored in memory 120 relating to indicator values 200 may be values obtained at a particular point in time, mean or median values, values over time, or the like. Similarly, threshold values 210, 220, 230 may be related to individual absolute values, mean or median values, values over time, or the like. In various embodiments, threshold vales 210, 220, 230 are based on monitored information regarding the indicator of infection. In some embodiments, processor 110 compares a determined first indicator metric 200 to a look-up table of threshold values 210, 220, 230 stored in memory 120 to determine whether the indicator is indicative of infection or if an action should be taken by device.

In some embodiments, processor 110 may compare an indicator metric 200 calculate threshold values 210, 220, or 230 based on information monitored within the patient by device 1. For example, a threshold value 210, 220, 230 may be deviation of 50% or greater, 40% or greater, 30% or greater, 20% or greater, 10% or greater, 5% or greater, etc. from a mean or median indicator value 200 monitored within the patient over a period of time. Alternatively, or in addition, such threshold values may be based on information received from an external device based on, e.g., patient data prior to implantation of device 1. Processor 110 may compare indicator metric 200 to a calculated threshold value 210, 220, 230. Of course, in such instances, processor 110 may compare indicator metric 200 to a mean or median indicator value 200 determined over time to determine whether a threshold has been crossed without first storing such threshold value 210, 220, 230 in memory 120.

It will be understood that the components described in FIGS. 1-7 are but examples of components that an implantable device 1 may have and that many other device or system configurations may be employed to carry out the methods described below. However, for the sake of convenience, the discussion that follows with regard to the methods illustrated in the flow diagrams of FIGS. 8-9 will refer to components as described with regard to FIGS. 1-7.

Figure 8A:
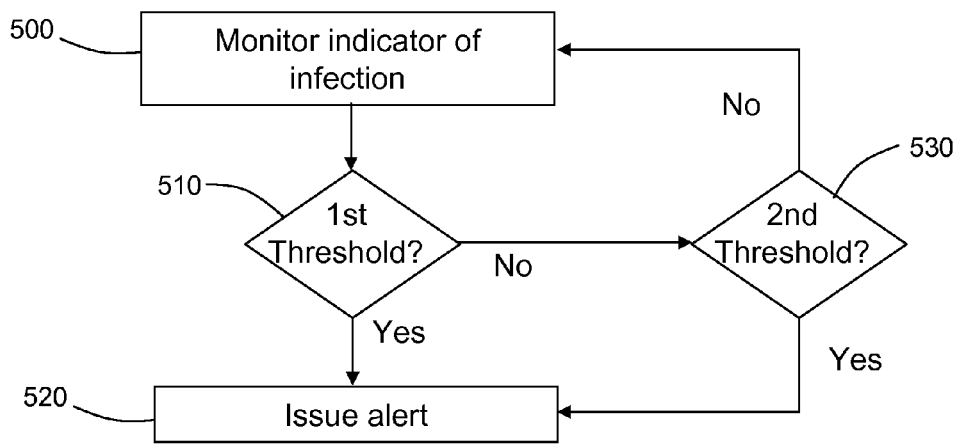
FIGS. 8-9 are flow diagrams of representative methods.
Figure 8B:
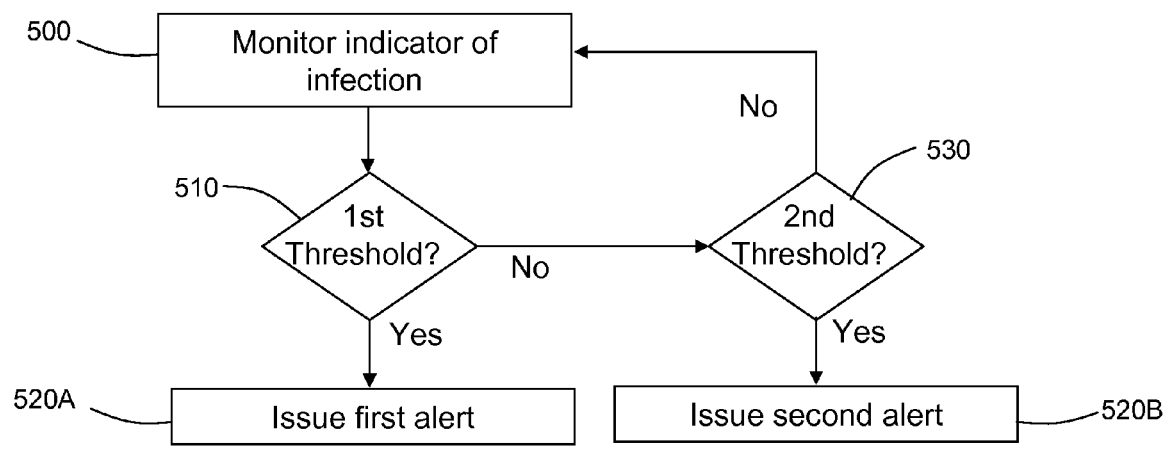

Referring to FIGS. 8A-B, flow diagrams of representative methods are shown. A method for monitoring an infection in proximity to a medical device includes monitoring an indicator of infection in proximity to a medical device implanted in a patient (500). Monitoring may include transmitting information from one or more sensor 50 to processor 110 or memory 120. The indicator may be monitored continuously or in discrete time intervals. The method further includes determining whether the monitored indicator crosses a first threshold indicative of infection for a first period of time (510). Processor 110 may determine whether the first threshold is crossed for the first period of time by comparing an indicator metric 200 stored in memory 120 with a first threshold value 210. If the first threshold 210 has been crossed by the monitored indicator, an alert may be issued (520). The first period of time may be a given point in time or a time period greater than a point in time. By way of example, the first threshold determination (510) may be whether a temperature of 103° F. (3.94 C) or greater has been detected at a given point in time, whether a temperature of 102° F. (38.9 C) has been detected over consecutive readings or for more than 30 minutes, etc. The alert may include a sensory indication, such as an audible indication or a tactile indication, such as a vibration, or visual indication. A visual indication may include, for example, text or an image. The alert may be issued by implanted device 1 or an external device 40 (see, e.g., FIG. 4), such as a programmer. If the indication is visual, the alert will be presented to the patient or clinician by an external device. If the indicator does not cross the first threshold, a determination is made as to whether the indicator crosses a second threshold for a second period of time (530), which is longer than the first period of time associated with the first threshold. As with the first threshold determination, the second threshold determination may include determining whether a value has been detected over consecutive discrete readings, continuously over time, etc. With the first or second determinations (510, 530), the determination may include whether a threshold value has been crossed over a percentage of the period of time; e.g. over 80% of the time in the time period, over 85% of the time in the time period, over 90% of the time in the time period, over 95% of the time in the time period, or the like. Alternatively, or in addition, the determination may include whether a threshold value has been crossed over a percentage of a number of readings within the time period; over 80% of the readings in the time period, over 85% of the readings in the time period, over 90% of the readings in the time period, over 95% of the readings in the time period, or the like. In various embodiments, a value associated with the second threshold 220 is less indicative a comparable value associated with the first threshold 210. By way of example, a temperature of 102° F. (38.9 C) may be less indicative of infection than a temperature of 103° F. (3.94 C). However, because the second time period associated with the second threshold is greater than the first time period associated with the first threshold, the presence of a less indicative value over an extended period of time may also be indicative of infection. If the second threshold is crossed over the second time period, an alert is issued (520).

If the second threshold is not crossed, the process of monitoring an indicator of infection (500), determining whether the first threshold has been crossed (510), determining whether the second threshold has been crossed (530) may continue. While not shown, it will be understood that the process or portions thereof may continue if an alert is issued (520). Alternatively, the process or portions thereof may be stopped to conserve power. As shown in FIG. 8B, a first alert may be issued (520A) if the first threshold is crossed (510) and a second alert may be issued (520B) if the second threshold is crossed (530). As shown in FIG. 8A, the first alert and the second alert may be the same.

Figure 9:
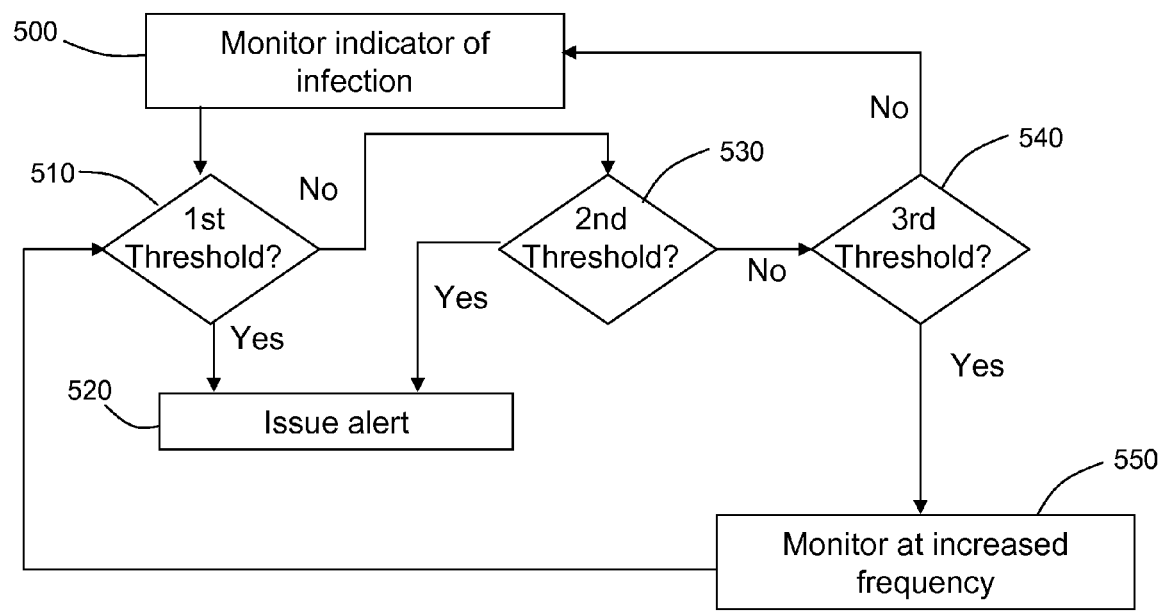

Referring to FIG. 9, an indicator of infection is monitored (500). The monitoring may occur over discrete time intervals. As with the embodiments depicted in FIGS. 8A-B, a determination is made as to whether the monitored indicator crosses a first threshold (510) and may include determining whether the monitored indicator crosses a second threshold (530). If the second threshold is not crossed, a determination is made as to whether a third threshold is crossed (540) for a third period of time. If the third threshold is met for the third period of time, the frequency with which the indicator is monitored is increased (550). In various embodiments, the third threshold over the third period of time is less indicative of an infection than the second threshold over the second period of time. Thus, detection of the third threshold value over the third period of time may not be sufficient to warrant issuing an alert (520), but may justify diverting power to increased monitoring due to increased likelihood of infection. Following the increased frequency of monitoring (550), the process of determining whether the first threshold is met (510), whether the second threshold is met (520), and whether the third threshold is met (530) may continue. If the third threshold is not met for the third period of time, monitoring may continue at the previous frequency (500).

The embodiments depicted in FIG. 9 may be desirable for active devices 1, as power consumption may be conserved. That is, power that may otherwise be used for providing therapy is not diverted to monitoring the indicator at increased frequency (550) until such information may be needed. Additional information regarding reduction of power consumption while monitoring infection is described in U.S. patent application Ser. No. 11/737,169, entitled "Event Triggered Infection Monitoring", naming Martin Gerber and John Rondoni as inventors; and U.S. patent application Ser. No. 11/737,170, entitled "Infection Monitoring", naming Martin Gerber and John Rondoni as inventors. The above-referenced patent applications are hereby incorporated herein by reference in their respective entireties to the extent that they do not conflict with the disclosure presented herein.

While not shown in FIGS. 8-9, a step of implanting device 1 may be included in the methods described herein.

Thresholds values, against which values associated with monitored indicators or parameters may be compared, will be apparent to skilled practioners or readily obtainable through routine experimentation. Additional information regarding use of thresholds determining infection in proximity to an implantable medical device is provided in U.S. patent application Ser. No. 11/737,181, entitled "Multi-Parameter Infection Monitoring", filed on even date herewith, naming Martin Gerber and John Rondoni as inventors, which application is hereby incorporated herein by reference in its entirety to the extent it does not conflict with the disclosure presented herein.

By way of example, some representative example thresholds values that may be used according to the methods described herein are provided below. For temperature, the first threshold may be greater than or equal to 101° F. (38.3 C) at a given point in time, greater, greater than or equal to 100.5° F. (38.1) over two consecutive readings, etc. The second threshold may be greater than or equal to 100° F. (37.8 C) over two hours, greater than or equal to 99.5° F. (37.5 C) over twelve hours, etc. The third threshold may be greater than or equal to 99° F. (37.2 C) at a given point in time, greater than or equal to 99.5° F. over two hours, greater than or equal to 100° F. over two consecutive readings, etc.

For pH, the first threshold may be, for example, greater than 7.7 or less than 6.5 at a point in time, a 10% deviation from a mean value at a point in time, etc. The second threshold may be, for example, greater than 7.6 or less than 6.6 over a period of two hours, a 5% deviation from a mean value over two hours, etc. The third threshold may be, for example, greater than 7.7 or less than 6.7 at a point in time, a 3% deviation from a mean value over two hours, etc.

For impedance, the first threshold may be, for example, a 30% deviation from a mean value at a point in time, a 25% deviation from a mean value over a twelve hour time period, etc. The second threshold may be, for example, a 20% deviation from a mean value over a 24 hour time period; the third threshold may be, for example, a 10% deviation from a mean value a 48 hour time period; etc.

For biological markers, the first threshold may be, for example, a 30% deviation from a mean value at a point in time, a 25% deviation from a mean value over a one hour time period, a 25% deviation from a mean value over three consecutive readings, etc. The second threshold may be, for example, a 20% deviation from a mean value over a two hour time period, a 20% deviation from a mean value over ninety percent of twenty consecutive readings, etc. The third threshold may be, for example, a 10% deviation from a mean value at a point in time, a 10% deviation from a mean value over a 60 minute time period, a 15% deviation from a mean value over two consecutive readings, etc.

Figure 10A:
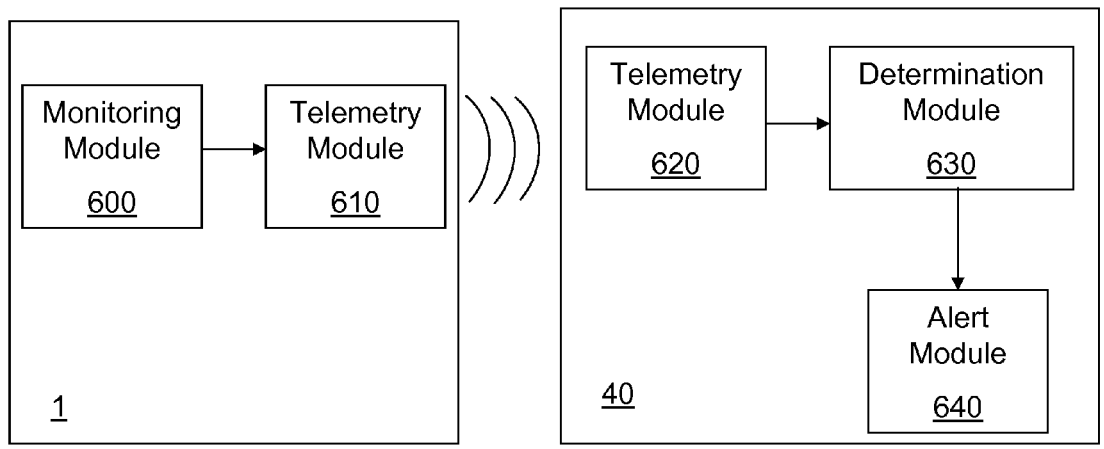
FIGS. 10A-D are schematic block diagrams of a representative implantable medical devices or systems.
Figure 10B:
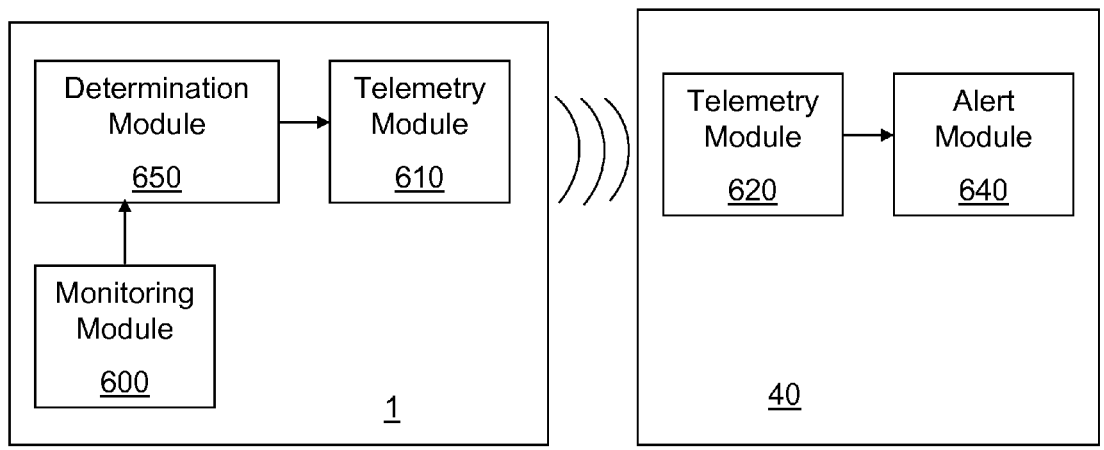
Figure 10C:
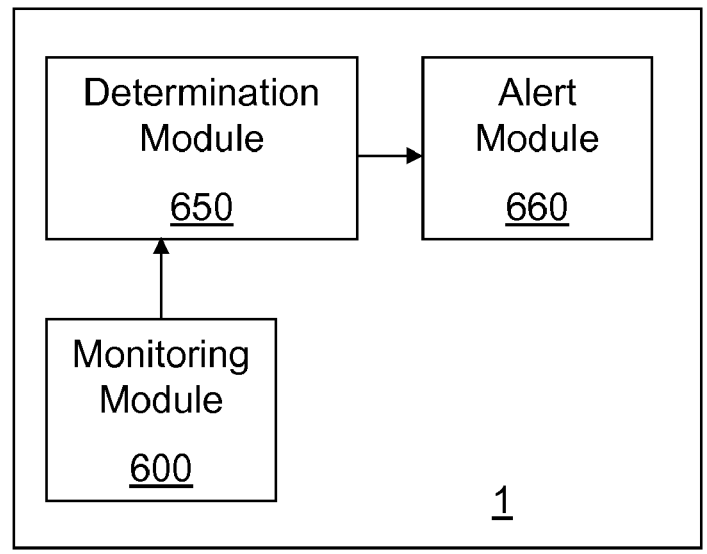
Figure 10D:
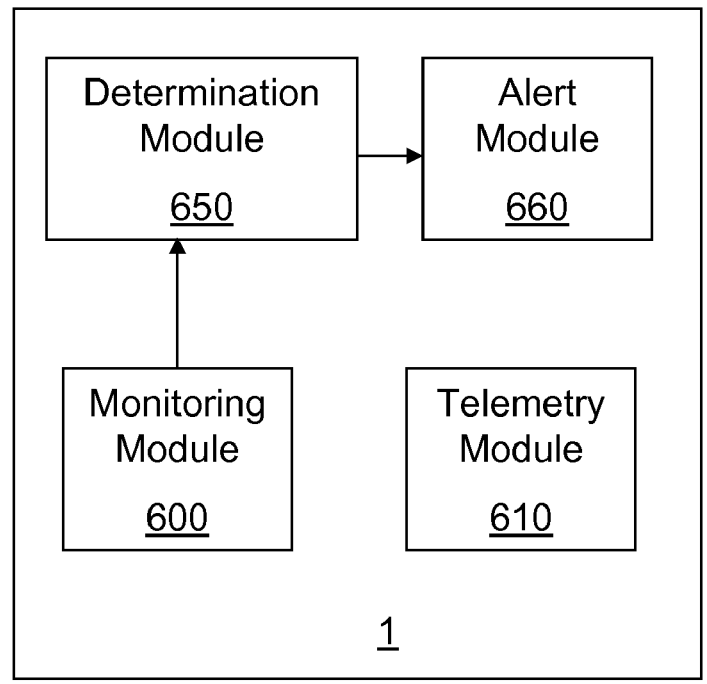

FIGS. 10A-D are block diagrams of representative devices or systems. It will be understood that one or more components described with regard to FIG. 6 may be included or carry out a function of one or more modules described in FIGS. 10A-D. As shown in FIGS. 10A-D, a system or device suitable for carrying out one or more method as discussed with regard to FIGS. 8-9 may include one or more monitoring module 600, telemetry modules 610, 620, a determination module 630, and an alert module 640. Monitoring module 600 includes sensor 50 and allows for sensed information to be provided to device 1 and may be saved in memory 120. Determination module 630 includes processor 110 that may determine, based on sensed information, whether an infection in proximity to device 1 is likely. If an infection is likely, alert module 640 may be used to issue an alert, e.g. prompting the patient to seek appropriate medical attention. Telemetry modules 610, 620 may be used to communicate information from implanted device 1 to external device 40 (or from external device 40 to internal device 1). As shown in FIGS. 10A-B, certain modules or portions thereof may be in implanted device 1 and certain modules or portions thereof may be in external device 40. As shown in FIGS. 10C-D, implanted device 1 may include sufficient components to carry out the methods described herein, whether or not device 1 includes a telemetry module 610 for communicating with external device 40.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause an implantable medical device (or system including an implantable medical device) to perform the methods described herein are contemplated. In an embodiment the computer readable medium contains instructions that when implemented cause an implantable medical device to (i) monitor an indicator of infection in proximity to an implanted medical device; (ii) determine whether the indicator crosses a first threshold indicative of infection for a first period of time; (iii) issue a first alert if the indicator crosses the first threshold for the first period of time; (iv) determine whether the indicator crosses a second threshold indicative of infection for a second period of time, a value associated with the second threshold being less indicative of an infection than a comparable value associated with the first threshold and the second period of time being greater than the first period of time; and (v) issue a second alert if the indicator crosses the second threshold for the second period of time. The first and second alert may be the same or different. Devices including the computer readable medium are also contemplated.

In addition, the principles of the methods, systems and devices described herein may be used for detecting various other potential adverse health issues associated with an implantable medical device. For example, temperature, pH, impedance, and various indicators of infection may also be used to determine whether a hematoma, edema, or seroma is present in proximity to an implanted device. Accordingly, monitoring of such other potential adverse health issues is within the scope of the present disclosure.

Patent applications directed to infection monitoring that may provide additional insight into the teachings provided herein include the following patent applications filed on even date herewith: (i) U.S. patent application Ser. No. 11/737,173, entitled "Infection Monitoring", naming Martin Gerber and John Rondoni as inventors; (ii) U.S. patent application Ser. No. 11/737,179, entitled "Controlling Temperature During Recharge for Treatment of Condition", naming Martin Gerber and John Rondoni as inventors; and (iii) U.S. patent application Ser. No. 11/737,176, entitled "Refined Infection Monitoring", naming Martin Gerber and John Rondoni as inventors. The above-referenced patent applications are hereby incorporated herein by reference in their respective entireties to the extent that they do not conflict with the disclosure presented herein.

Thus, embodiments of INDICATOR METRICS FOR INFECTION MONITORING are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for alerting that an infection is likely to be present in proximity to an implanted medical device, the method comprising: using the implanted medical device to monitor an indicator of infection in proximity to the implanted medical device; determining whether a metric of the indicator crosses a first threshold indicative of infection for a first period of time;
  determining whether the metric of the indicator crosses a second threshold indicative of infection for a second period of time, the second threshold being less indicative of an infection than the first threshold and the second period of time being greater than the first period of time; and
  issuing an alert if
    (i) the metric of the indicator crosses the first threshold indicative of infection for the first period of time, or
    (ii) the metric of the indicator crosses the second threshold indicative of infection for the second period of time.

2. The method of claim 1, wherein the first or second threshold is an absolute value metric.

3. The method of claim 1, wherein the first or second threshold is a percent deviation from a mean value metric.

4. The method of claim 1, wherein monitoring the indicator of infection comprises monitoring the indicator in discrete time intervals at a first frequency range.

5. The method of claim 4, further comprising:
  determining whether the metric of the monitored indicator crosses a third threshold for a third period of time; and
  increasing the frequency with which the indicator is monitored if the metric of the monitored indicator crosses the third threshold for the third period of time.

6. The method of claim 1, wherein determining whether the metric of the indicator of infection crosses the second threshold comprises comparing information regarding the indicator obtained in discrete time intervals.

7. The method of claim 6, wherein issuing the alert comprises issuing the alert if the indicator crosses the second threshold in consecutive discrete time intervals.

8. The method of claim 1, wherein determining whether the metric of the indicator crosses the first threshold for the first period of time comprises determining whether the metric of the indicator crosses the threshold for a predetermined percentage of the first time period, and wherein the alert is issued if the indicator crosses the first threshold for the predetermined percentage of the first time period.

9. The method of claim 1, wherein determining whether the metric of the indicator crosses the second threshold for the second period of time comprises determining whether the metric of the indicator crosses the threshold for a predetermined percentage of the second time period, and wherein the alert is issued if the metric of the indicator crosses the threshold for a predetermined percentage of the second time period.

10. The method of claim 1, wherein monitoring the indicator of infection comprises monitoring temperature in proximity to the implanted medical device.

11. The method of claim 10, wherein determining whether the metric of the indicator crosses the first threshold for the first period of time comprises determining whether the temperature at any given time is greater than 101° F.

12. The method of claim 11, wherein determining whether the metric of the indicator crosses the second threshold for the second period of time comprises determining whether the temperature is above 100° F. for two hours or more.

13. The method of claim 1, wherein monitoring the indicator of infection comprises monitoring pH in proximity to the implanted medical device.

14. The method of claim 1, wherein determining whether the metric of the indicator crosses the first threshold comprises determining whether the pH has deviated from a mean value by greater than 10%.

15. The method of claim 1, wherein determining whether the metric of the indicator crosses the second threshold comprises determining whether the pH has deviated from a mean value by greater than 5%.

16. The method of claim 1, wherein monitoring the indicator of infection comprises monitoring impedance in proximity to the implanted medical device.

17. The method of claim 1, wherein determining whether the metric of the indicator crosses the first threshold comprises determining whether the impedance has deviated from an average impedance value more than 30%.

18. The method of claim 1, wherein determining whether the metric of the indicator crosses the second threshold comprises determining whether the impedance has deviated from an average impedance value more than 20%.

19. A computer readable medium comprising instructions that when implemented cause an implantable medical device to:
   monitor an indicator of infection in proximity to an implanted medical device;
   determine whether a metric of the indicator crosses a first threshold indicative of infection for a first period of time;
   determine whether the metric of the indicator crosses a second threshold indicative of infection for a second period of time, the second threshold being less indicative of an infection than the first threshold and the second period of time being greater than the first period of time; and
   issue an alert if
      (i) the metric of the indicator crosses the first threshold indicative of infection for the first period of time, or
      (ii) the metric of the indicator crosses the second threshold indicative of infection for the second period of time.

20. An implantable medical device comprising:
   the computer readable medium of claim 19;
   electronics capable of executing instructions of the computer readable medium;
   a sensor capable of detecting the indicator of infection and providing the electronics with information regarding the indicator; and
   an alarm operably coupled to the electronics and configured to provide the alert.

21. The method of claim 4, further comprising:
   increasing the frequency with which the indicator is monitored if the metric of the monitored indicator crosses the second threshold.

* * * * *